United States Patent [19]
Siess et al.

[11] Patent Number: 6,007,478
[45] Date of Patent: Dec. 28, 1999

[54] CANNULA HAVING CONSTANT WALL THICKNESS WITH INCREASING DISTAL FLEXIBILITY AND METHOD OF MAKING

[75] Inventors: Thorsten Siess, Aachen; Helmut Reul, Düren; Günter Rau; Jens Hutzenlaub, both of Aachen, all of Germany; Peter Brown, Palo Alto, Calif.

[73] Assignee: Impella Cardiotechnik Aktiengesellschaft, Aachen, Germany

[21] Appl. No.: 08/970,135

[22] Filed: Nov. 13, 1997

[51] Int. Cl.[6] .......................... A61N 1/362; A61M 25/01
[52] U.S. Cl. .................. 600/16; 600/585; 604/282
[58] Field of Search ............. 600/16, 585; 604/280–282

[56] References Cited

U.S. PATENT DOCUMENTS

| | | |
|---|---|---|
| 5,061,256 | 10/1991 | Wampler . |
| 5,112,349 | 5/1992 | Summers et al. . |
| 5,221,270 | 6/1993 | Parker ........................................ 604/282 |
| 5,376,114 | 12/1994 | Jarvik . |
| 5,533,985 | 7/1996 | Wang . |
| 5,701,905 | 12/1997 | Esch ......................................... 600/585 |
| 5,704,926 | 1/1998 | Sutton ...................................... 604/280 |
| 5,725,513 | 3/1998 | Ju et al. ................................... 604/280 |
| 5,769,828 | 6/1998 | Jonkman . |
| 5,792,124 | 8/1998 | Horrigan et al. . |
| 5,827,242 | 10/1998 | Follmer et al. . |
| 5,911,685 | 6/1999 | Siess et al. . |

*Primary Examiner*—William E. Kamm
*Assistant Examiner*—Carl H. Layno
*Attorney, Agent, or Firm*—Fulwider Patton Lee & Utecht, LLP

[57] ABSTRACT

A cannula for use as for example on the inflow end of an implantable intravascular heart pump. The stiffness of the cannula is differentiated along its length, wherein its proximal end is stiffer than its distal end, while a substantially constant wall thickness is maintained along its entire length. Attached to the flexible distal end, is a rigid tip component having inlet ports and an interior surface profile that minimizes the risk of hemolysis and thrombogenisis.

42 Claims, 4 Drawing Sheets

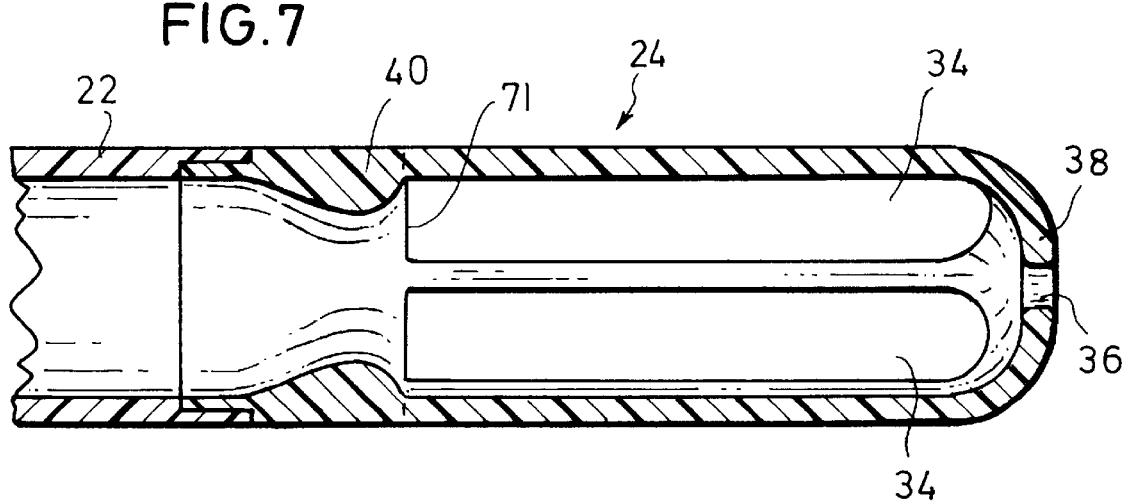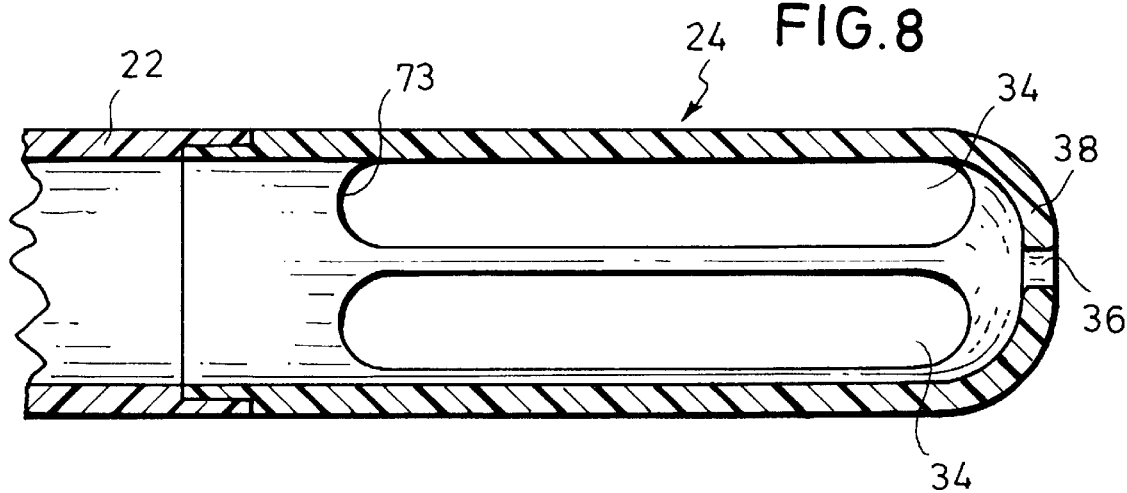

CANNULA HAVING CONSTANT WALL THICKNESS WITH INCREASING DISTAL FLEXIBILITY AND METHOD OF MAKING

BACKGROUND OF THE INVENTION

The present invention generally relates to cannulas and more particularly pertains to cannulas suited for applications requiring a high degree of maneuverability as well as the ability to accommodate high blood flow rates therethrough with minimal blood damage.

Cannulas must often be able to satisfy a number of competing requirements. In applications such as for example, the inflow cannula of an implantable intravascular heart pump, the inner diameter of the cannula must be as large as possible in order to accommodate the extremely high flow rates inherent in such application. On the other hand, the outer diameter of the cannula should be as small as possible in order to enable it to be maneuvered through the convolutions of the patient's vasculature, for example around the aortic arch through the aortic valve and into the heart. Moreover, a smaller outer diameter minimizes the size of the puncture that must be made in the vasculature in order to gain access thereto. Additionally, the cannula must be stiff enough to allow its distal end to be routed through vasculature by manipulation of its proximal end, yet flexible enough to conform to the vasculature and not injure the tissue it comes into contact with. Blind retrograde insertion into for example, the left ventricle through the aortic valve is especially problematic in that an advancing cannula has a natural tendency to enter the sinus region adjacent the valve leaflet and become jammed rather than retrogradely passing through the periodically opened valve. Additionally, because substantial flow velocities and possible suction pressures may be involved, the risk of shear or cavitation must be addressed while the presence of a foreign body within the blood flow poses a risk of thrombogenisis especially in flow stagnant areas.

Cannulas have been previously devised in an attempt to satisfy the requirements associated with heart pump applications but have fallen short of overcoming many of the difficulties involved. The importance of preventing the radial collapse of the cannula had been recognized and consequently a spiral spring had previously been incorporated in some cannulas. On the other hand, in order to render the distal end as soft as possible, the spiral spring was terminated somewhat short of the distal end and while this does soften the distal end, the section of cannula sans spring was then prone to kinking, and consequently flow obstruction. The flexible tip is also subject to being sucked against parts of the vasculature or ventricular apparatus and can subsequently collapse to block the flow of fluid therethrough. In an effort to simultaneously impart the necessary flexibility and rigidity to the cannula, the wall thickness of hereto known cannulas has been varied along its length. By significantly increasing wall thickness near the proximal end, the necessary forces can be transmitted without sacrificing the flexibility needed at the distal end. However, while this imparts the desired stiffness differentiation, it has the undesired side effect of either significantly increasing the cannula's maximum external diameter or decreasing its minimum internal diameter. Additionally, the entrance ports formed in heretofore known cannulas have failed to take into consideration the substantial blood flow velocities that may be forced therethrough and the injury that may be sustained by the blood due to the abrupt directional changes that are encountered.

A cannula configuration is needed that is sufficiently soft and sufficiently rounded at the distal end to prevent injury yet not prone to collapse or wall suction. Moreover, the cannula must be sufficiently resistant to deformation to ensure maneuverability without sacrifice to its flow capacity. Blood flow into and through the cannula must be managed so as to minimize damage to the blood while minimizing pressure losses therewithin. Heretofore known cannulas have failed to adequately address these requirements.

SUMMARY OF THE INVENTION

The cannula of the present invention overcomes many of the shortcomings of previously known configurations and is especially well suited for but not limited to use in implantable intravascular heart pump applications both as an inflow as well as an outflow conduit. Attached to the distal end of such a device, it enables the assembly to be more easily maneuvered throughout a patient's vasculature and facilitates its blind retrograde insertion past a heart valve while minimizing injury to tissue and leaflets. Once in place, the cannula accommodates maximum blood flow rates with a reduced amount of shear, turbulence and risk of cavitation to thereby minimize blood damage.

The cannula of the present invention consists of a cylindrical body component of constant diameter and substantially constant wall thickness, wherein its resistance to lateral deflection is nonetheless differentiated along its length. More specifically, the distal end is more flexible than its proximal end, wherein the transition between the different flexibility characteristics may either be gradual or abrupt. An abrupt change is achieved by simply joining two materials of disparate flexibility as in a butt joint or a stepped joint. A gradual transition is achieved by employing a composite construction wherein the relative content of a relatively more flexible material gradually displaces more and more of a stiffer material as the distal end is approached. In a preferred embodiment, two materials of differing flexibility are layered and their relative thicknesses are gradually varied while their total thickness is held substantially constant. The stiff proximal end of the cannula is either attached to the pump housing of the associated intravascular pump or is configured to actually serve as the impeller housing. Such alternative configuration not only reduces the number of parts that must be separately assembled but additionally smooths the transition between the pump housing and cannula so as not to disrupt blood flow.

An additional feature incorporated in the body of the cannula is an embedded spiral spring which imparts resistance to radial deformation. Of critical importance is the use of a spring material that readily regains its shape even after having been subjected to significant deformation to thereby ensure that the patency of the cannula is maintained. In an alternative embodiment, the function of the spring may be served by a metallic tube incorporated within the cannula that has an advantageous pattern of voids formed therein. By for example, laser cutting the tube so as to define a spiral of varied spacing between adjacent windings and/or of windings of varied widths, the tube serves to simultaneously impart a varying degree of flexibility to the tube while preventing its radial deformation. Similar effect is achievable with various patterns of voids formed in the tube wherein the density of the void pattern at any given position along its length is determinative of the structure's flexibility as such position.

Disposed at the distal end of the cannula body is a rigid tip component that includes a number of features that serve

3 to overcome the disadvantages inherent in previously known cannula tips. The tip is formed of a substantially non-collapsible material having a number of openings formed therein. The openings are formed on all sides of the component and are of sufficient size such that the complete blockage of one such opening, as would occur if the tip becomes positioned against the heart or vessel wall, does not significantly compromise the flow capacity of the cannula. In addition to the sizing of the openings, the openings are configured so as to minimize the risk of wall suction. This is achieved by elongating the openings along the length of the tip in order to minimize the possibility of even a single opening becoming entirely occluded. The elongated openings may additionally be angled relative the central axis to achieve a somewhat helical configuration. To minimize the risk of tissue or leaflet damage, the distal end of the tip is substantially closed and well rounded. An orifice is additionally centrally formed therein to accommodate a guide wire should one be used for the placement of the device. The rigid tip is either formed separately and attached to the flexible distal end of the cannula or is formed as part of the cannula wherein the cannula's stiffness is abruptly increased near its distal end.

In the event the cannula is to be used for inflow applications, the inner wall adjacent the downstream edges of the orifices is shaped so as to manage the flow of blood thereabout. By either rounding the downstream edge configuration or forming a parabolic protuberance along the edge of a squared off orifice, shear is prevented and the flow of blood is smoothly attached to the interior wall to prevent eddying. The risk of hemolysis and thrombogenisis is thereby greatly reduced. In the event the cannula is to be used for outflow applications, flow characteristic out through the tip may be enhanced with the modification of the interior volume so as to define a parabolic cone extending proximally along the central axis. The base of the cone joins the walls of the tip component immediately adjacent the distal-most reach of the openings. Additionally, the openings may be extended into the rounded region of the distal end of the tip component.

Finally, a monitoring device such as a pressure sensor may be embedded in the cannula in order to provide information regarding the condition of the patient and/or operation of the blood pump. The sensor as well as any electrical conduits necessary for its operation are incorporated in the wall of the device during its fabrication.

The fabrication of the cannula of the present invention is generally accomplished by assembling the various components about a mandrel such as by successively coating layers of material of differing stiffness thereon. By varying the distribution of successive layers of the selected materials and/or the width of the spiral spring structure, the desired stiffness differentiation is achieved. Other components such as a stiffening component, a spiral spring and sensors are incorporated in the wall of the cannula by their placements between layers of the successively applied material.

These and other features and advantages of the present invention will become apparent from the following detailed description of preferred embodiments which, taken in conjunction with the accompanying drawings, illustrate by way of example the principles of the present invention.

4

Figure 2:
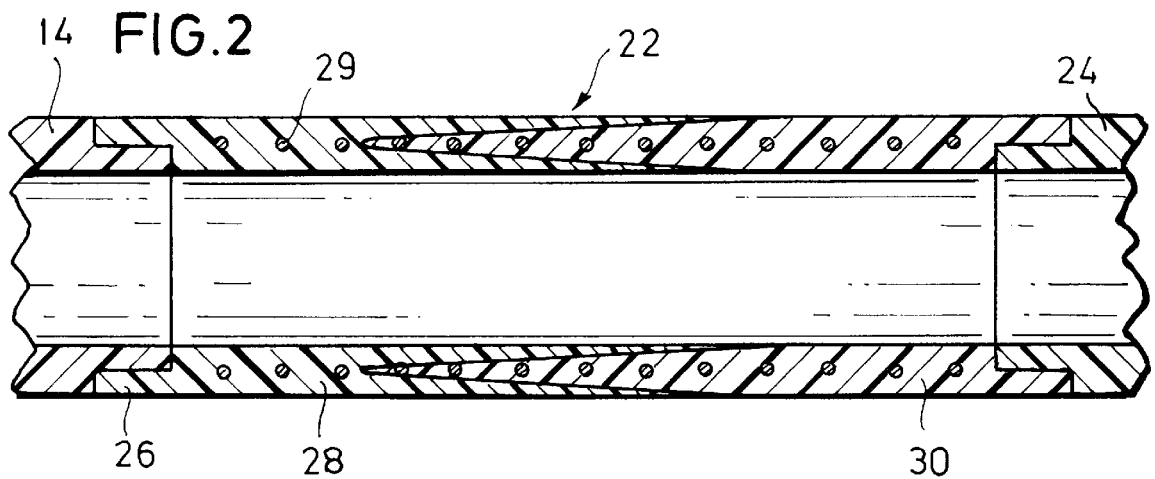
Figure 3:
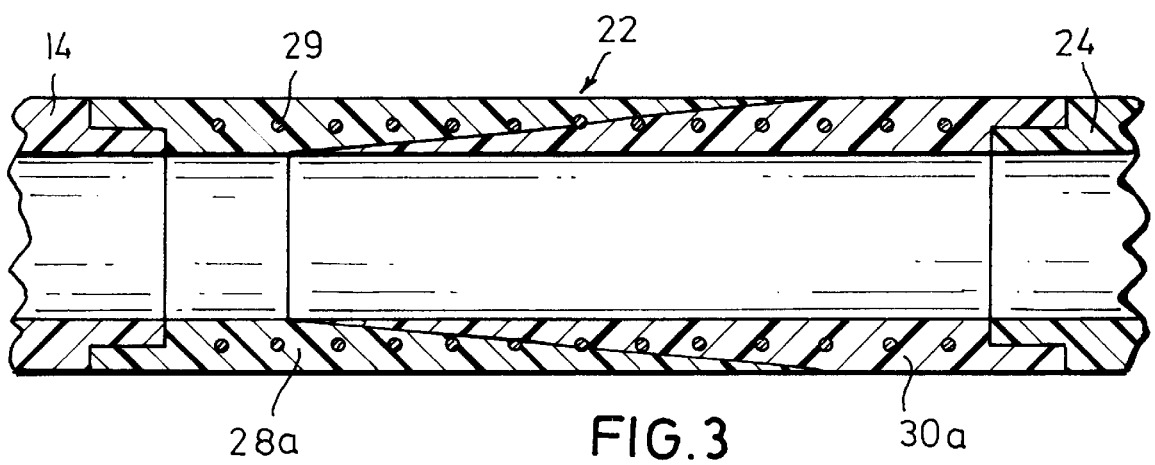
Figure 4:
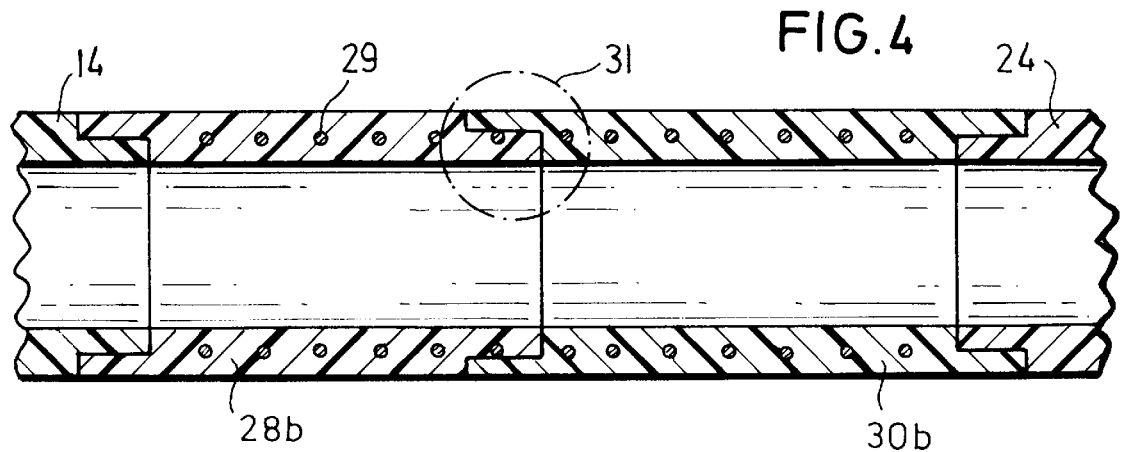
Figure 5:
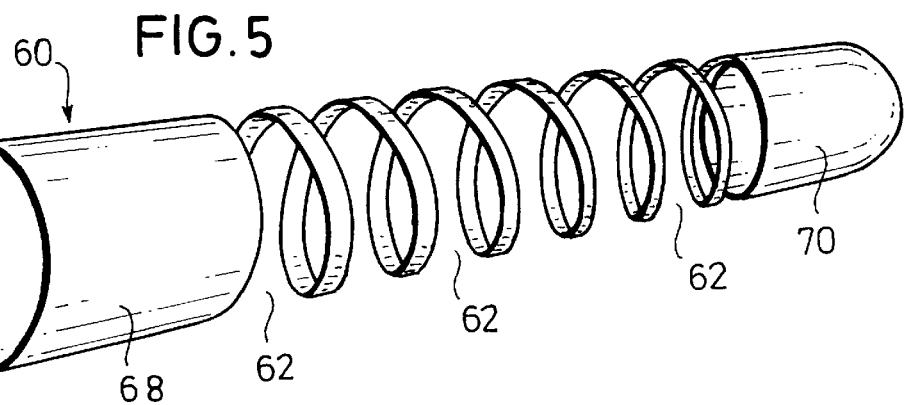
Figure 6:
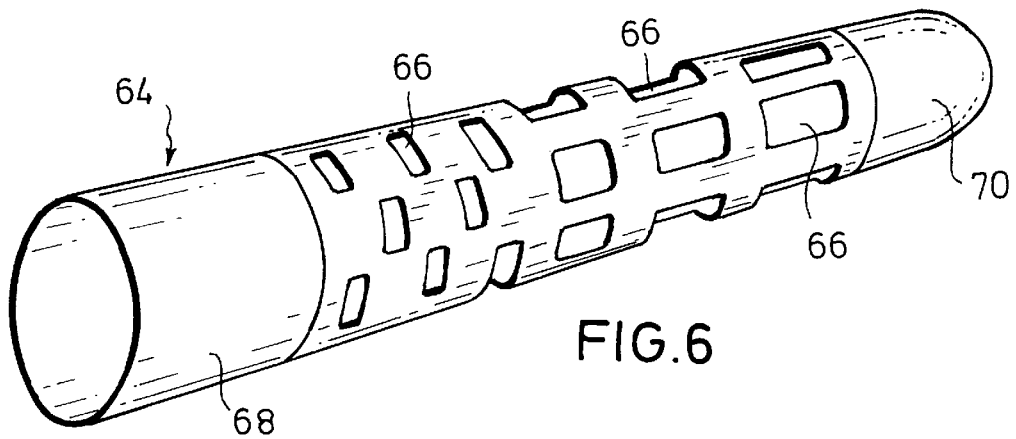
Figure 9:
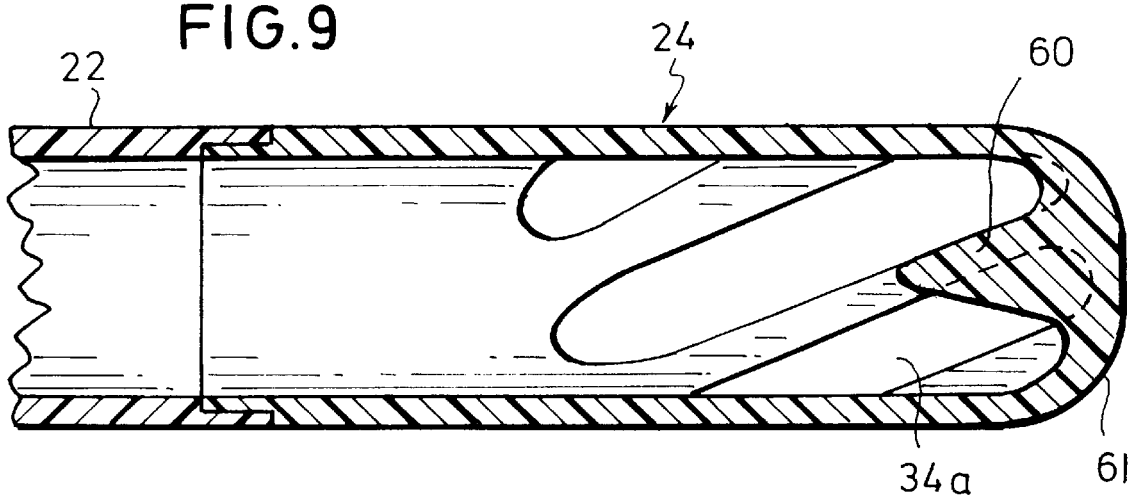
Figure 10:
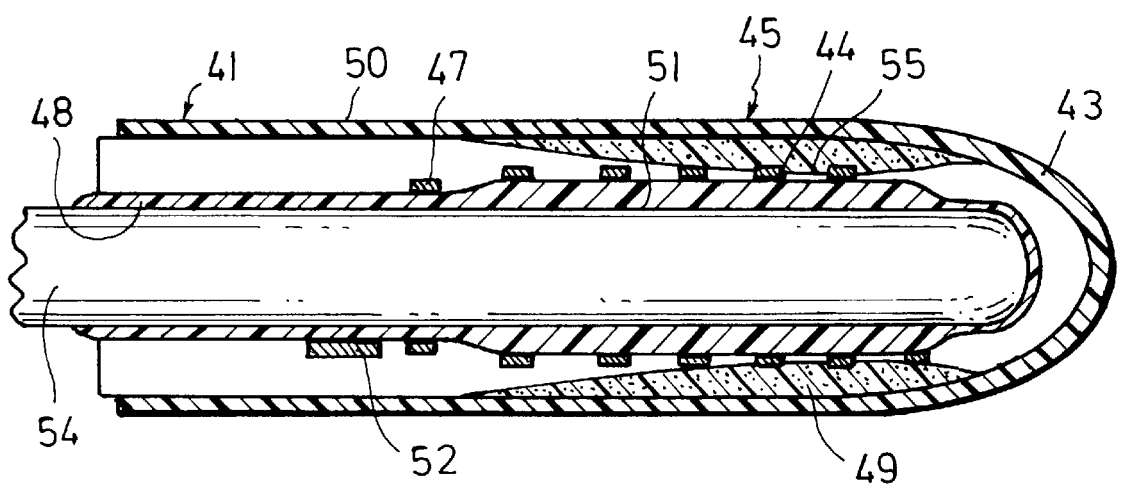

FIG. 2, is greatly enlarged, longitudinally compressed, cross-sectional view of the body component of the cannula of the present invention;

FIG. 3, is a greatly enlarged, longitudinally compressed, cross-sectional view of the body component of an alternative embodiment of the present invention;

FIG. 4, is a greatly enlarged, longitudinally compressed, cross-sectional view of the body component of another alternative embodiment of the present invention;

FIG. 5, is a greatly enlarged perspective view of stiffening component for incorporation within a alternative embodiment cannula of the present invention;

FIG. 6, is a greatly enlarged perspective view of an alternative embodiment stiffening component;

FIG. 7, is a greatly enlarged, cross-sectional view of the tip component of the cannula of the present invention;

FIG. 8, is a greatly enlarged cross-sectional view of an alternative embodiment tip component;

FIG. 9, is a greatly enlarged cross-sectional view of another alternative embodiment tip component; and FIG. 10, is a greatly enlarged, longitudinally compressed, cross-sectional view of an alternative embodiment of the present invention.

DETAILED DESCRIPTION OF PREFERRED EMBODIMENTS

The figures generally illustrate the cannula of the present invention. The cannula is most advantageously used as an inflow conduit on the distal end of an implantable intravascular heart pump. In such application it serves to enhance maneuverability through the vasculature and upon placement, accommodates extremely high flow rates with a minimum of adverse effects to the pumped blood. The cannula provides similar advantages when used as an outflow conduit.

Figure 1:
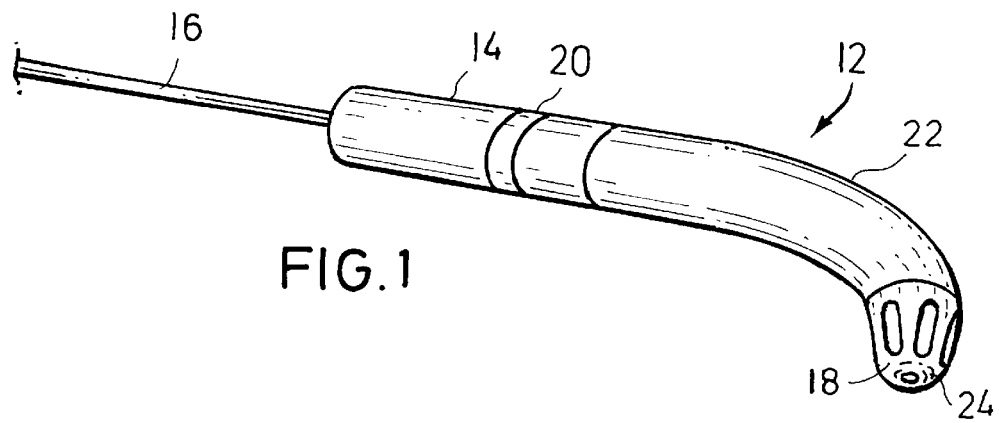
FIG. 1, is a perspective view of the cannula of the present invention attached to the distal end of an implantable intravascular flow pump.

FIG. 1 is a perspective view showing the cannula 12 attached to the distal end of an implantable intravascular blood pump 14. Manipulation of a catheter 16 extending from the proximal end of the pump allows the assembly to be maneuvered through the vasculature to the pumping site such as for example up through the femoral artery, around the aortic arch and with the tip extending into the left ventricle. For such application, the outer diameter of the cannula must be limited to about 8 mm while its length must be sufficient to ensure that the pump's discharge port 20 is located clear of the aortic valve even while the tip 18 of the cannula is bottomed out in the left ventricle of a large patient (about 8 cm). Similar dimensions are appropriate for right ventricle applications wherein the distally disposed cannula serves as an outflow conduit. The cannula device of the present invention very generally consists of a body component 22 of differentiated flexibility and a rigid tip component 24.

FIG. 2 is enlarged, longitudinally compressed, cross-sectional view of the body portion 22 of the cannula 12 of the present invention. A rigid pump housing 14 is attached at its proximal end while rigid tip 24 is attached thereto at its distal end. On each end, the components are engaged in a stepped 26 fashion and are permanently bonded to one another. The body component has a constant wall thickness along its entire length and is formed as a layered composite of two materials, one relatively stiff 28, the other relatively more flexible 30. A similar effect can be achieved with the use of two materials of identical chemical composition, albeit with different physical characteristics, such as a polyurethane with different degrees of polymerization. The layers are arranged such that the thickness of one material gradually diminishes as the other increases. In the embodiment illustrated in FIG. 2, this is achieved by the flexible material being formed with a generally wedged cross-sectional configuration 30 which is received in a complementarily shaped cavity formed in the stiffer material. Other complementary configurations are similarly feasible as for example shown in FIG. 3 wherein a simple ramping of one material 28a relative to the other 30a achieves a similar differentiation of stiffness. FIG. 4 illustrates an embodiment wherein an abrupt change in flexibility is achieved by joining two materials of differentiated flexibility 28b, 30b in a stepped fashion at 31. In either case, at the proximal end of the cannula body, its composition comprises substantially 100% of the stiffer material while at the distal end, the composition comprises substantially 100% of the more flexible material. The stiffer material may consist of any number of materials including but not limited to a polyurethane or resin impregnated fibers while the more flexible material may consist of any number of materials including but not limited to a silicone compound. The two different materials may in fact comprise the same chemical composition yet be differentiated in terms of for example, degree of polymerization or crystallinity. Two forms of a polyurethane for example, may be combined in accordance with the present invention to yield a flexibility differentiated cannula.

Embedded within the wall of the body structure is a spiral spring 29 of for instance, NiTi wire. The presence of the spring imparts significant resistance to radial deformation while the particular alloy employed allows the spring to regain its original shape even after a substantial deformation that it may be subjected to during placement or manipulation of the heart. The spring wire may have any number of cross-sectional shapes including but not limited to round or rectangular cross-sections with the further option of varying axial density in order to change the elasticity or flexibility of the cannula.

Alternatively, resistance to radial deformation is achieved with the incorporation of a metal tube 60 within the cannula's cylindrical wall, wherein such tube has a pattern of voids 62 formed therein such as by laser cutting. Such voids may be patterned to form a helix similar in appearance to the spiral spring described above. As is shown in FIG. 5, the pattern of voids cut into the tube may additionally be differentiated along its length such that the tube's resistance to lateral deflection is commensurately varied. FIG. 6 illustrates a further alternative of tubular stiffening component 64 wherein a pattern of rectangular voids 66, varied in terms of size of distribution density imparts the desired differentiation in terms of flexibility. In both embodiments, the proximal end is solid and thus its stiffness in uncompromised to enable it to serve as a pump housing while the distal end 70 is similarly solid to serve as reinforcement of the tip component to provide for maximal rigidity. The tube 60, 64 thereby serves to simultaneously provide radial stiffness and a varying degree of resistance to lateral deflection. In an alternative embodiment, differentiated flexibility is achieved exclusively via the laser cut metal tube while the polymer makeup of the cannula is unvaried along its length.

FIGS. 7 and 8 illustrates the rigid tip component 24 of the cannula. Such component may be a separate injection molded part or alternatively, may be of integral construction and incorporates a number of features especially advantageous for high inflow rate applications. A number of large elongated openings 34 extend along its length, while a central hole 36 at the very distal end is sized to accommodate a guide wire. The distal end 38 is smooth and rounded without additional openings to prevent injury upon contacting tissue, and/or valve leaflets.

In the embodiment shown if FIG. 7, the interior surface of the tip component directly adjacent the squared off proximal or inflow end 71 of openings 34 is formed with an edge contour 40 of generally parabolic cross-section that serves to manage the flow of blood thereabout. The shape not only presents a rounded surface at the point of initial contact with the incoming blood, but additionally serves to smoothly attach the flow of blood to the interior wall with its asymptotic trailing edge contour. As a result, the risk of excessive shear and cavitation is minimized to thereby minimize the risk of hemolysis while areas of eddying or of low flow rates are substantially eliminated to thereby mitigate the risk of thrombogenisis. Similar advantages may be achieved by rounding the downstream edges 73 of the openings as shown in FIG. 8. Such configuration provides the advantage of being easily molded.

FIG. 9 illustrates an alternative embodiment especially well suited for outflow applications. As is visible in the cross-sectional view, the distal end of the interior volume of the tip component is fitted with a generally parabolic protuberance 60 extending proximally along the central axis. Such element directs flow out through the openings 34a and effectively prevents flow impingement onto a closed distal wall. The resulting reduction in eddying and areas of stagnant flow reduces thrombogenisis. The embodiment additionally illustrates a slanted orientation of the openings 34a as well as their extension well into the rounded distal area 61.

FIG. 10 illustrates an alternative embodiment that incorporates a number of additional features not present in the embodiments shown in the preceding figures. The device is of integrated construction such that the rigid proximal end of the cannula forms the pump housing 41 while the flexible distal end seamlessly transitions into the rigid tip component 43. No joints or bonds are formed and thus, the seamless transitions from the tip 43 to the cannula 45 and from the cannula 45 to the pump housing 41 effectively obviate any disruption of bloodflow thereover. The desired differentiations in stiffness are achieved by the varied content of epoxy impregnated fibers windings 47 incorporated within the structure. By closely spacing such fibers, and thereby displacing all of a second substantially more flexible material, maximum strength is achieved. Such strength is sufficient to in fact satisfy the strength requirements for the pump housing and the tip component. Conversely, increased spacings between adjacent fiber windings provides additional space for the accommodation of an increased amount of flexible material 49 and thus increased flexibility is achieved at such points along the length of the cannula.

A layer of biocompatible material 48, 50 coats both the internal as well as external surfaces of the device. The thickness of the internal layer is increased 51 under the spiral spring 44 so as to preclude migration of such spring into the blood flow. The spring wire shown in FIG. 9 is of rectangular construction to thereby minimize the wall thickness of the device which is constant along its entire length. The proximal end of the spring is incorporated well within the fiber windings. In this embodiment, a sensor 52 is incorporated in the wall of the device. In some applications it is desirable to monitor any of a number of parameters at such location for the purpose of gauging the patient's condition and/or the performance of, for example, the associated pump.

The fabrication of the device illustrated in FIG. 10 is achieved by first applying a layer 48 of biocompatible polymer such as polyurethane to a highly polished mandrel 54. The thickness of the layer is increased 51 slightly near where the spiral spring 44 is to be subsequently positioned in order to prevent migration of the spring into the fluid path. Pre-impregnated carbon fiber filaments 47 are then wound about the coated mandrel at an approximate 45° angle to ensure good stability against axial and radial deformation. The spacing of successive windings is controlled such that the fiber content is maximized in those areas where maximum stiffness is desired, i.e., the pump housing and tip component. Such spacing is gradually increased in those areas where gradually more flexibility is desired. Areas 55,where maximum flexibility is desired are totally devoid of fibers. After curing, the outside surface is machined down to its final dimension and the ports are formed in the tip component 43. Layers of an elastic polymer 49 such as polyurethane or silicone are then applied in order to fill the areas between adjacent fibers and the spring windings. A final layer 50 of biocompatible polymer is applied to the exterior of the entire device to render all surfaces biocompatible. After all materials have cured, the finished device is slipped off the mandrel 54.

In an alternative embodiment, the tip component 24, is fabricated separately such as by injection molding. The tip is then either attached by adhesive or by solvent bonding. A final layer of biocompatible polymer may then be applied to the assembly to render its surfaces biocompatible and to fill in any gaps that may be present along the joints between adjacent components.

In an alternative embodiment, a single stiffening component comprising the pump housing, cannula and tip are fashioned from a single metal tube having a varying pattern of voids formed therein such as by laser cutting. Since the density of voids at any given point along its length determines the resulting flexibility of the structure at such point, no voids or a minimum of voids are formed in the pump housing and tip sections of the device while a pattern of voids is formed therebetween to impart an increasing degree of flexibility to the cannula's body component. The surfaces of the tube and the voids therebetween are subsequently coated and filled with a polymer in a fashion as described above.

In use, the cannula of the present invention, attached to the distal end of an implantable intravascular blood pump, is inserted into the femoral artery and maneuvered upwardly toward the heart. Alternatively, the device may be inserted directly into the aorta via a sternotomy. The flexible distal end permits the device to negotiate the convolutions of the artery including the aortic arch. The increased stiffness of the proximal end permits adequate axial and torsional forces to be transmitted to the tip to enhance control thereof and thereby facilitate proper advancement of the device. Blind retrograde insertion through the aortic valve is accomplished by simply advancing the tip until the valve is engaged. Should the tip attempt to enter while the aortic valve is open, it will simply pass into the left ventricle. On the other hand, should the tip attempt to enter while the aortic valve is closed, it will engage the sinus region behind the leaflet, while further advancement will cause the flexible region near the cannula's distal end to fold over to allow a more proximal and stiffer section of the cannula to breach the valve first. Alternatively, upon feeling resistance the device can be pulled back and reinserted. Once inside, the cannula has room to unfold and is ready for service. A similar technique is used for right side placement.

Once in position, fluid is drawn into the ports in the tip's distal end and such flow is smoothly attached to the inner wall by the presence of parabolic protrusions or curved inflow edge. Shear, cavitation and turbulence is thereby minimized resulting in reduced hemolysis and thrombogenisis. Should the tip component be situated in abutment with the wall of the ventricle, sufficient port area will remain exposed so as not to compromise the flow rate through the cannula. The size of each port, by virtue of its elongation additionally minimizes the pressure drop thereacross and thus the risk of wall suction.

While a particular form of the invention has been illustrated and described, it will also be apparent to those skilled in the art that various modifications can be made without departing from the spirit and scope of the invention. For example, various combinations of materials can be used to achieve the differentiated stiffness along the cannula's length and various layering configurations can be used to vary the relative amounts of material. Additionally, the cannula is not limited to any particular use. In addition to use as an inflow conduit on the distal end of an implantable intravascular heart pump, many other applications are feasible. Accordingly, it is not intended that the invention be limited except by the appended claims.

What is claimed is:

1. A cannula for conducting the flow of fluid therethrough and for facilitating its routing through vasculature, comprising:

a cylindrical body component of substantially constant wall thickness having a gradually varying degree of resistance to lateral deflection wherein its proximal end is stiffer than its distal end and wherein the proximal end includes and an impeller housing; and a support structure disposed within the wall of said cylindrical body component imparting resistance to radial collapse.

2. The cannula of claim 1 wherein the body component is constructed of at least two materials comprising a first relatively stiff material and a second relatively flexible material and wherein the relative content of said two materials is varied along the length of said body component.

3. The cannula of claim 2 wherein said two materials have identical chemical compositions but differing durometer hardnesses.

4. The cannula of claim 2 wherein said two materials comprise discrete layers.

5. The cannula of claim 4 wherein each of said layers is of gradually varying thickness along its length.

6. The cannula of claim 4 wherein each of said layers is of constant thickness and the number of layers of each material is varied along the length of said cannula.

7. The cannula of claim 4 wherein said two materials comprise polyurethane and silicone.

8. The cannula of claim 2 wherein said first material comprises windings of fibers.

9. The cannula of claim 8 wherein said fibers are of variable density along the length of said cannula.

10. The cannula of claim 8 wherein said fibers comprise resin impregnated kevlar.

11. The cannula of claim 10 wherein said second material comprises a polyurethane.

12. The cannula of claim 1 wherein said support structure comprises spirally configured spring material.

13. The cannula of claim 12 wherein said spring material comprise NiTi alloy.

14. The cannula of claim 1 further comprising a rigid hollow tip component attached to the distal end of said body component.

15. The cannula of claim 14 wherein said tip component has a smooth and rounded distal end.

16. The cannula of claim 14 wherein said tip component has a plurality of orifices formed therein.

17. The cannula of claim 16 wherein said orifices have an elongated shape and have an arrangement along the longitudinal axis.

18. The cannula of claim 17 wherein said tip has a rounded distal end and said orifices extend into said rounded end.

19. The cannula of claim 16 wherein said orifices are elongated and have an angled position relative to the longitudinal axis.

20. The cannula of claim 19 wherein said tip has a rounded distal end and said orifices extend into said rounded end.

21. The cannula of claim 16 wherein said tip component has a guidewire hole formed therein.

22. The cannula of claim 16 wherein an inwardly protruding parabolic restriction is formed about the trailing edge of each orifice.

23. The cannula of claim 16 wherein each orifice has a trailing edge and wherein each such edge is rounded.

24. The cannula of claim 16 wherein each orifice has a trailing edge and wherein such trailing edge is parabolically shaped.

25. The cannula of claim 16 wherein a parabolic protrusion extends proximally within said tip along its longitudinal axis and engages said tip component adjacent the distal ends of said orifices.

26. The cannula of claim 1 further comprising a sensor incorporated said body component.

27. The cannula of claim 1 further comprising a layer of biocompatible material covering all internal and external surfaces.

28. The cannula of claim 1 wherein a metal tube comprises said support structure and wherein said metal tube has voids formed therein of varying shape and size so as to impart said varying degree of resistance to lateral deflection.

29. The cannula of claim 28 wherein said tube has voids formed therein so as to define a spiral of varying spacings.

30. The cannula of claim 28 wherein said tube has voids formed therein so as to define a spiral of varying width.

31. A cannula for conducting the flow of fluid therethrough and for facilitating its routing through vasculature, comprising:
    a cylindrical body component of substantially constant wall thickness and differentiated flexibility along its length wherein its distal end is more flexible than its proximal end; and
    a hollow, rigid tip component disposed at the distal end of said body component having a plurality of orifices formed therein.

32. The cannula of claim 31 wherein said body component and tip component are of integral construction.

33. The cannula of claim 31 wherein the proximal end of said body component comprises an impeller housing.

34. The cannula of claim 33 wherein said body component and impeller housing are of integral construction.

35. The cannula of claims 33 wherein said body component, tip component and impeller housing are of integral construction.

36. A method of constructing a cannula of differentiated stiffness comprising the steps of:
    selecting a mandrel;
    applying a layer of biocompatible material thereto;
    winding fibers about said biocompatible material wherein the density of such windings is increased in those areas where increased stiffness is desired; and
    applying flexible material thereover to form a structure of constant wall thickness along its entire length.

37. The method of claim 36 wherein winding fibers involves concentrating the density of the fibers at the proximal end of said cannula and gradually decreasing the density toward the distal end.

38. The method of claim 37 wherein the proximal end of said cannula forms a pump housing.

39. The method of claim 37 wherein winding fibers involves concentrating the density of the fibers near the distal end of said cannula to form a rigid tip component.

40. A method of constructing a cannula of differentiated stiffness comprising the steps of:
    selecting a mandrel;
    applying a layer of biocompatible material thereto;
    selecting a metal tube dimensioned for receipt over said biocompatible material applied to said mandrel;
    forming voids in said tube by laser cutting so as to impart a desired pattern of differentiated flexibility therealong;
    positioning said tube over said biocompatible coated mandrel; and
    applying flexible material to form a structure of constant wall thickness.

41. A method of constructing a cannula of differentiated stiffness comprising the steps of:
    selecting a mandrel;
    applying a layer of biocompatible material thereto;
    selecting a metal tube formed of NiTi and dimensioned for receipt over said biocompatible material applied to said mandrel;
    forming voids in said tube so as to impart a desired pattern of differentiated flexibility therealong;
    positioning said tube over said biocompatible coated mandrel; and
    applying flexible material to form a structure of constant wall thickness.

42. A cannula for conducting the flow of fluid therethrough and for facilitating its routing through vasculature, comprising:
    a cylindrical body component of substantially constant wall thickness having a gradually varying degree of resistance to lateral deflection wherein its proximal end is stiffer than its distal end;
    a support structure disposed within the wall of said cylindrical body component imparting resistance to radial collapse; and
    a rigid hollow tip component attached to the distal end of said body component.

* * * * *

UNITED STATES PATENT AND TRADEMARK OFFICE
CERTIFICATE OF CORRECTION

PATENT NO. : 6,007,478
DATED : December 28, 1999
INVENTOR(S) : Siess et al.

It is certified that error appears in the above-identified patent and that said Letters Patent is hereby corrected as shown below:

Column 8, line 66, delete "14" and insert --42--; and

Column 9, line 1, delete "14" and insert --42--.

Signed and Sealed this

Twenty-ninth Day of August, 2000

Attest:

Attesting Officer

Q. TODD DICKINSON
Director of Patents and Trademarks